US008261601B2

(12) United States Patent
Stolle et al.

(10) Patent No.: US 8,261,601 B2
(45) Date of Patent: Sep. 11, 2012

(54) TOP OF THE LINE CORROSION APPARATUS

(75) Inventors: Joseph W. Stolle, Wharton, TX (US); Dylan V. Pugh, Manvel, TX (US); David A. Norman, Houston, TX (US); Wei Sun, Houston, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 282 days.

(21) Appl. No.: 12/606,781

(22) Filed: Oct. 27, 2009

(65) Prior Publication Data

US 2010/0147056 A1    Jun. 17, 2010

Related U.S. Application Data

(60) Provisional application No. 61/122,224, filed on Dec. 12, 2008.

(51) Int. Cl.
*G01N 17/00* (2006.01)
(52) U.S. Cl. ............................ 73/86; 422/53; 422/68.1
(58) Field of Classification Search ......... 73/86; 422/53
See application file for complete search history.

(56) References Cited

U.S. PATENT DOCUMENTS

| | | | |
|---|---|---|---|
| 3,056,664 A | 10/1962 | Dravnieks et al. | |
| 3,936,273 A | 2/1976 | Powell | |
| 3,996,124 A | 12/1976 | Eaton et al. | 204/195 |
| 4,179,920 A | 12/1979 | Schuller et al. | |
| 4,267,148 A | 5/1981 | Dickson et al. | 422/53 |
| 4,282,181 A | 8/1981 | Pierce | |
| 4,335,072 A * | 6/1982 | Barnett et al. | 422/53 |
| 4,563,427 A | 1/1986 | Weiss et al. | 436/6 |
| 4,611,175 A | 9/1986 | Kumar et al. | 324/425 |

(Continued)

FOREIGN PATENT DOCUMENTS

WO    WO2008/115050    9/2008

OTHER PUBLICATIONS

Author: Ziru Zhang, Title: A Study of Top of the Line Corrosion Under Dropwise Condensation, Date: Mar. 2008, Publisher: the Russ College of Engineering and Technology of Ohio University, pp. 1-73.*

(Continued)

*Primary Examiner* — Lisa Caputo
*Assistant Examiner* — Roger Hernandez-Prewitt
(74) *Attorney, Agent, or Firm* — ExxonMobil Upstream Research Company Law Department

(57) ABSTRACT

The described invention relates to a method for determining corrosion in wet gas pipelines comprising: a) using a portion of the liquid phase from a wet gas pipeline; b) placing said portion in a high pressure, high temperature autoclave to prepare a saturated vapor phase; c) transferring the saturated vapor to a corrosion test unit, said unit having a specimen holder section having external, temperature adjustable means, and specimens being arranged in one or more positions within the specimen holder; d) chilling said specimen holder section so as to cause condensation onto said corrosion testing specimens; and, e) calculating a value selected from the group consisting of corrosions rate, pitting of the specimen, weight loss of the specimen, and any combination thereof. The invention process can be practiced in a separate laboratory apparatus designed to accomplish the above method, or in a similar online apparatus set up in a semi-batch mode or continuous mode.

17 Claims, 3 Drawing Sheets

U.S. PATENT DOCUMENTS

| | | | |
|---|---|---|---|
| 4,711,131 A | | 12/1987 | Hopkins |
| 5,254,310 A | * | 10/1993 | Bressan .......................... 422/53 |
| 5,425,267 A | | 6/1995 | Herrmann et al. |
| 5,517,851 A | | 5/1996 | Berthold et al. ................... 73/87 |
| 5,531,103 A | | 7/1996 | Eaton |
| 6,264,824 B1 | | 7/2001 | Reid et al. ................... 205/775.5 |
| 6,693,445 B1 | | 2/2004 | Sutton .......................... 324/700 |
| 6,843,135 B2 | | 1/2005 | Douglas et al. |
| 7,127,959 B2 | | 10/2006 | Blum et al. |
| 7,141,150 B1 | | 11/2006 | Welch et al. |
| 7,148,706 B2 | | 12/2006 | Srinivasan et al. ............ 324/700 |
| 7,185,531 B2 | | 3/2007 | Souers |
| 7,561,976 B2 | | 7/2009 | Bernard et al. ................. 702/42 |
| 7,609,874 B2 | | 10/2009 | Eswara et al. ................ 382/149 |
| 7,818,156 B2 | | 10/2010 | Vachhani et al. ............... 703/12 |
| 2007/0261842 A1 | | 11/2007 | Gillet et al. |
| 2008/0163692 A1 | | 7/2008 | Huang et al. .................... 73/627 |

OTHER PUBLICATIONS

Bendiksen, K. H. et al., "The Dynamic Two-Fluid Model OLGA: Theory and Application", SPE 19451, SPE Production Engineering, May 1991, pp. 171-180.

Freeman, E. N. et al., "New Technology Effective in Reducing Top-of-The-Line Corrosion Rate", Pipeline & Gas Journal, Jan. 2007, pp. 44-47.

Freeman, E. N. et al., "Top of Line Corrosion Rate Reduction Using V-Jet™ Inhibitor Dispersal Pig", T. D. Williamson, Inc., 2006, 9 pages.

Gunaltun, Y. et al., "Interpretation of MFL and UT Inspection Results in Case of Top of Line Corrosion", $61^{st}$ Annual NACE International Conference (Corrosion 2006), Mar. 12-16, 2006, pp. 1-15, San Diego, CA.

Gunaltun, Y. M. et al., "Top-of-The-Line Corrosion Conclusion—Models updated; remediation strategies set out", Oil & Gas Journal, Jul. 17, 2000, pp. 68-71.

Gunaltun, Y. M. et al., "Top-of-line corrosion in gas lines confirmed by condensation analysis", Oil & Gas Journal, Jul. 12, 1999, pp. 64-71.

Gunaltun, Y. M. et al., "Top-of-Line Corrosion—Water condensation rate critical", Oil & Gas Journal, Jul. 10, 2000, pp. 58-63.

Mendez C. et al., "Effect of Acetic Acid, pH and MEG on the CO2 Top of the Line Corrosion", $60^{th}$ Annual NACE International Conference (Corrosion 2005), Apr. 3-7, 2005, pp. 1-27, Houston, TX.

Nyborg, R. et al., "Prediction of top of line corrosion in wet gas pipelines", European Federation of Corrosion Reliability Management of Technical Systems Congress (Eurocorr 2006), Sep. 25-28, 2006, Maastricht, The Netherlands.

Vitse, F. et al., "Mechanistic Model for the Prediction of Top-of-The-Line Corrosion Risk", Paper No. 03633, Annual NACE International Conference (Corrosion 2003), Mar. 16-20, 2003, pp. 1-19, Houston, TX.

European Search Report, Oct. 7, 2009, 6 pages.

\* cited by examiner

TOP OF THE LINE CORROSION APPARATUS

CROSS REFERENCE TO RELATED APPLICATIONS

This application claims the benefit of U.S. Provisional Application No. 61/122,224, filed Dec. 12, 2008.

FIELD OF INVENTION

This invention relates generally to assessing and controlling top of the line corrosion occurring in wet natural gas pipelines.

BACKGROUND OF THE INVENTION

Natural gas is becoming a very attractive fuel from both environmental and economic perspectives. In most instances of recovery from its source in its natural state, the natural gas will be relatively warm from its subterranean locations, and "wet", that meaning that it will contain moisture. Transportation of natural gas from its source thus can be as dry gas transportation, where the gas is dehydrated prior to transporting in a pipeline, or directly as wet gas transportation before dehydrating. Dry gas transportation is preferred since it can avoid a series of problems caused in wet gas transportation, such as, internal corrosion and hydrate formation. This approach does however require that drying process facilities be located near the source. However, significant numbers of natural gas reservoirs are located offshore, which requires costly offshore facilities to dehydrate the wet gas to dry gas Therefore, wet gas direct transportation from offshore reservoirs to onshore facilities can result in a significant cost savings. This direct transportation is generally conducted in transportation pipelines that are called "wet gas pipelines". These pipelines can be large in diameter, upwards of 30" (76.2 cm.) diameter, and in use have a substantial gas volume in the upper portion of the wet gas pipelines. But in addition, a small amount of liquids (water, condensate, and dissolved acid gases) are often present as a liquid phase at the bottom of the pipeline, and even sometimes as entrained moisture particles within the gas volume.

Further, since wet gas pipelines contain moisture laden gas, water can condense out near the top and upper sides of the pipeline when heat transfer occurs due to temperature gradients between that of the warm wet gas and the ambient pipeline temperature when routed through cold surroundings, such as subsea or arctic locations, etc. Wet gas pipelines are typically constructed of alloy steel for strength/cost reasons, and corrosion is often experienced to occur at both the bottom and the top of the pipe. Corrosion at the top of the pipeline occurs due to the above condensation on the exposed pipeline surface, and will be referred to herein as "Top of the Line Corrosion" (TOLC or TOL corrosion). The corrosion at the bottom of the pipeline is due to the liquids flowing along the bottom of the gas pipeline and will be referred to herein as "Bottom of the Line Corrosion" (BOLC or BOL corrosion). Both TOLC and BOLC will depend on the temperature variation between the gas in the pipeline and the outside temperature (affecting the condensation rate) and the additional presence of naturally occurring acid gases in the natural gases, such as $CO_2$, $H_2S$, and organic acids. TOLC can be more severe than BOLC since condensed liquid at the top of the pipeline cannot be easily or effectively modified with corrosion inhibitors that can be used at the bottom of the lines.

Thus mitigating TOL corrosion in wet gas pipelines is challenging. As noted above, corrosion inhibitor chemicals can be injected into wet gas pipelines to mitigate BOL corrosion that occurs due to the flow of condensed liquids and/or water at the bottom of the pipeline. However, it is difficult to continuously apply inhibitors to the top of the line especially in a stratified flow regime, where water or liquids with inhibitor only flow at the bottom of the line. So, in areas where pipeline condensation occurs, TOL corrosion is typically more severe. This is because of more aggressive water chemistry top of the line, coupled with an inability to effectively treat, that occurs with the stratified flow regime found in wet gas pipelines.

There are several existing strategies for mitigating TOL corrosion. First, batch corrosion inhibition may be used, where a slug of inhibited liquids is pushed through the line with one or more "pigs", solid objects sized to fit closely within the pipeline. In this approach, the corrosion inhibitor is delivered to the top of the pipe because the liquid slug largely fills the pipe ahead of the pig. To be effective, this method of batch corrosion inhibition must be conducted at regular intervals to reapply the corrosion inhibitor. Second, the pipeline may be operated in a flow regime where entrained liquid is delivered to the top of the pipe (e.g., slug flow and/or increased gas flow rates). In this approach, there must be enough inhibitor in the entrained liquid to mitigate corrosion at the top of the pipe and the pipeline must be operating at high flow rates. Third, one or more sections of the pipeline may be constructed from or lined with a corrosion resistant alloy (CRA) and located where the majority of the condensation occurs, for example at the entrance to the pipeline at the source. The remainder of the pipeline may be constructed from carbon or low alloy steel if the condensation rates in other regions are low enough to reduce the occurrence of TOL corrosion.

Developing methods and apparatus for testing or monitoring TOL corrosion of wet gas pipelines is very important. Top of the line corrosion testing may be used to measure corrosion rates for the design of wet gas pipelines and to identify mitigation strategies. Top of the line corrosion monitoring devices may be used to confirm that mitigation strategies are working or as guidance for determining inspection intervals of wet gas pipelines. Typical corrosion testing apparatus, such as atmospheric cells, high pressure, high temperature (HPHT) autoclaves, or flow loops, do not adequately represent the top of the line conditions. In these types of tests, corrosion coupons, specimens and/or probes are generally submersed in an aqueous solution and exposed to the partial pressures of the acids gases. This lead to a much greater solution volume to pipeline surface area than would be present at the top of an operating or flowing pipeline and does not accurately reproduce the condensation phenomenon. Further, it has proven difficult to accurately capture the key features of the top of the line corrosion in laboratory equipment so a need exists in the art to address this difficulty.

SUMMARY OF THE INVENTION

The invention method is one for determining corrosion in wet gas pipelines comprising: a) collecting or replicating a portion of the liquid phase from a wet gas pipeline; b) placing said portion in a high pressure, high temperature autoclave along with equivalent partial pressures of acid gases, and heating it to prepare a saturated vapor phase within said autoclave; c) transferring at least a portion of the saturated vapor to a corrosion test unit comprising a gas inlet port, a specimen holder section, one or more corrosion testing specimens arranged in said specimen holder section, a liquid collection outlet port, and a gas return line via a variable speed pump to the autoclave of a), said specimen holder section having external, temperature adjustable means; d) chilling said specimen holder section so as to cause condensation from said vapor phase onto said corrosion testing specimens; and, e) calculating a value selected from the group consisting of corrosions rate, pitting of the specimen, weight loss of the specimen, and any combination thereof. In a further embodiment, the invention process is one wherein the specimen holder is configured to allow specimens to be inserted in different orientations that simulate a portion of the pipeline selected from the group consisting of a top portion of the pipeline, a side portion of the pipeline, a bottom portion of the pipeline, and any combination thereof. An additional embodiment comprises draining and withdrawing at least a portion of the vapor after subjected to condensation chilling in the corrosion test unit for return to the autoclave via the variable speed pump. Optionally, this method can additionally comprise measuring the volume of said condensation in a liquid collection and measuring unit connected at the inlet side said unit to the outlet port before returning said condensation via said pump to said autoclave. A further embodiment additionally comprises halting periodically the flow of vapor from the autoclave to the corrosion testing unit, and measuring said corrosion testing plates for calculating the one or more values of step e), and replacing with new specimens or specimen section as needed.

In one or more preferred embodiments the process uses an apparatus suitable for determining corrosion in wet gas pipelines comprising: a) a high pressure, high temperature autoclave; b) a corrosion test unit comprising a gas inlet port, a specimen holder section, at least one corrosion testing specimen affixed in said specimen holder section, a liquid collection outlet port, and a gas return line via a variable speed pump to the autoclave a), said specimen holder section having external, temperature adjustable means, and said at least one specimen being arranged in one or more positions within said specimen holder section at the top, at various side positions, and the bottom; c) the variable speed pump; and, d) optionally, a liquid collection and measuring unit connected at the inlet side said unit to the outlet port in b) and at the inlet side to said variable speed pump.

BRIEF DESCRIPTION OF THE DRAWINGS

The present invention and its advantages will be better understood by referring to the following detailed description and the attached drawings in which.

The invention will be described below in connection with its preferred embodiments. However, to the extent that the following detailed description is specific to a particular embodiment or a particular use of the invention, this is intended to be illustrative only, and is not to be construed as limiting the scope of the invention. On the contrary, it is intended to cover all alternatives, modifications and equivalents that may be included within the invention as defined by the appended claims.

DETAILED DESCRIPTION OF PREFERRED EMBODIMENTS

Figure 1:
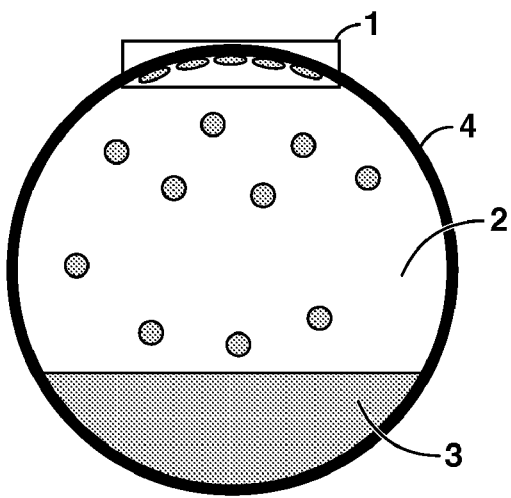
FIG. 1 is a cross-sectional view of a typical wet gas pipeline comprising a condensation area, a vapor phase and a liquid phase.

As shown in FIG. 1, a wet gas pipeline 4 will include a zone of TOL corrosion 1 occurring from condensing moisture from a vapor phase 2, and a liquid phase 3 along the bottom.

Figure 2:
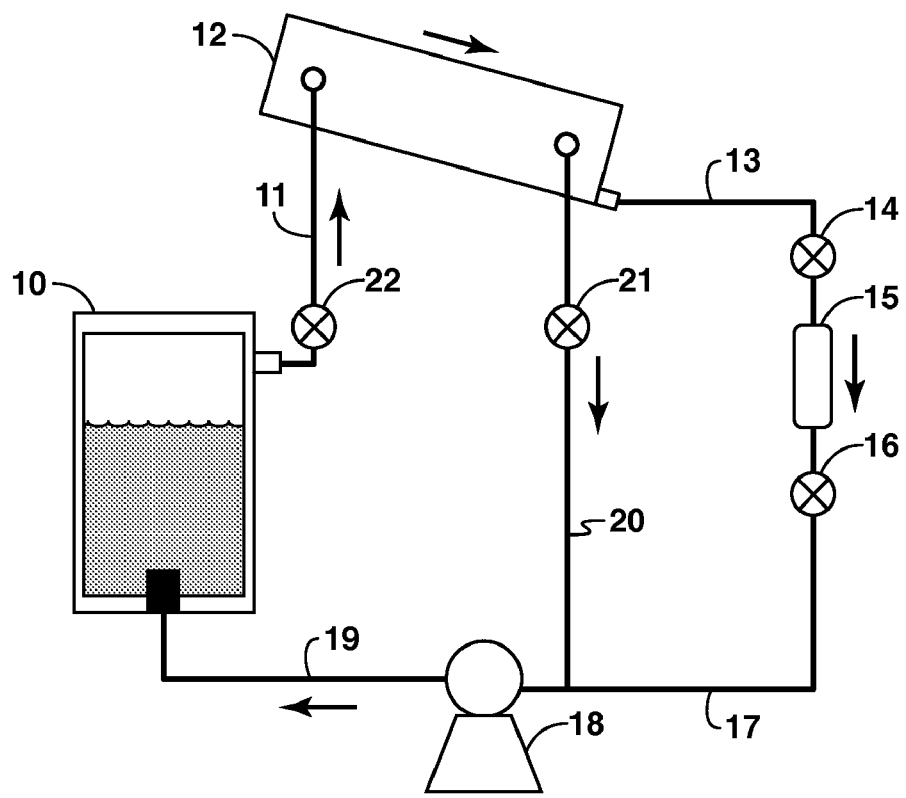
FIG. 2 is a diagram of a stand-alone invention apparatus that can be used in a laboratory.

A preferred laboratory process according to the invention comprises steps illustrated in the process/apparatus diagram of FIG. 2. The direction of flow is indicated by arrows. Deoxygenated liquids and acid gases ($CO_2$ and/or $H_2S$) are introduced to the apparatus through the HPHT (High Pressure/High Temperature) autoclave 10. These materials are as sampled from a gas pipeline, or replicated from such liquids. Typically analysis of the natural gas is conducted at the source or shortly thereafter, from which the moisture content and equivalent partial pressures of acid gases can be determined. Such pipeline partial pressures will typically vary from less than 1 psi to greater than or equal to 300 psi. By "equivalent", we mean that the partial pressures of the acid gases added corresponds to that present in the wet gas being transported. These liquids are then heated in autoclave 10 to a temperature set at a target gas temperature, e.g., one from the well-head or in the natural gas reservoir, or as experienced along other targeted positions along the path of travel through the pipeline, thus forming a saturated vapor phase. This vapor phase is then transferred via line 11 to a TOLC test section 12. Test section 12 comprises chilling specimens (coupons) inside that condense liquids from the saturated vapor. See FIG. 4 and following discussion for more detail. The temperature of the corrosion specimens or coupons is controlled to be approximately at the ambient temperature where corrosion is being determined, and is assumed to be the pipe wall temperature. See the example set out in Table 1, below. Test section 12 may be oriented as suitable to encourage flow, for example, tilted to allow easy removal of fluids. The vapor phase, minus its condensed liquids, is returned to the autoclave for re-saturation via line 20 and variable speed pump 18. Optional cutoff valve 21 can be used to stop the flow of vapor for shutdowns or servicing of pump 18. The condensed liquids (condensate) withdrawn from an outlet port of test section 12 can be disposed of, returned directly to autoclave 10, optionally, via pump 18, or as depicted, or can be provided via line 13 for measuring the condensate volume in volumetric measuring device 15, typically a sight glass, and calculating the condensation rate. The measured volume of condensate over a fixed period of time is used to calculate the condensation rate on the specimen. Optionally, analysis of the chemical make-up of a condensate sample can be conducted if desired on a sample of the withdrawn condensate, for example, through an additional sampling port (not shown) on measuring device 15. The condensate is then returned via lines 17 and 19, optionally via pump 18 as depicted, to the autoclave 10 for mixture with the liquids therein. One or more adjustments of gas and/or coupon/specimen temperature(s), to obtain a target condensation rate set to replicate that at the position in the pipeline where corrosion is to be determined, can be applied while running tests. Such can be determined through modeling or by observing conditions at the selected pipeline position. The process of the preceding steps is to be repeated for a period of time to achieve steady state results. The process can then be halted, and the coupons/specimens removed from the TOLC test section 12, inspected and measured for corrosion.

A target condensation rate for a specific locations in the pipeline can be calculated for modeling purposes from the temperature differential across the pipe wall (from measurements of ambient temperature and flowing gas temperature), the heat transfer characteristics of the pipe (including any coatings or insulation), and the vapor composition and flow rate. This target can then be used to adjust the temperatures in the invention process.

Typically the TOLC test section is assembled with one or more corrosion coupons or specimens that have been weighed and then inserted into a coupon holder. In a preferred embodiment, the specimens are arranged in one or more positions within said specimen holder section at the top, at various side positions, and, optionally, the bottom. When testing is complete the TOLC section is disassembled and the coupon(s) are removed. They are then weighed to measure weight loss corrosion rates and are examined for pitting corrosion. Other methods of measuring for corrosion can be used alternatively, or together, and are known to those skilled in the art. Mention may be made of measuring before and after use the change in physical size of the coupons or specimens. In an alternative embodiment, the "coupon holder" may be a single specimen, one which would be in a ready shape to be cooled, as above, and essentially be a sacrificial structural element in the shape of a specimen or coupon holder that is subjected to gas vapor-induced corrosion.

Figure 3:
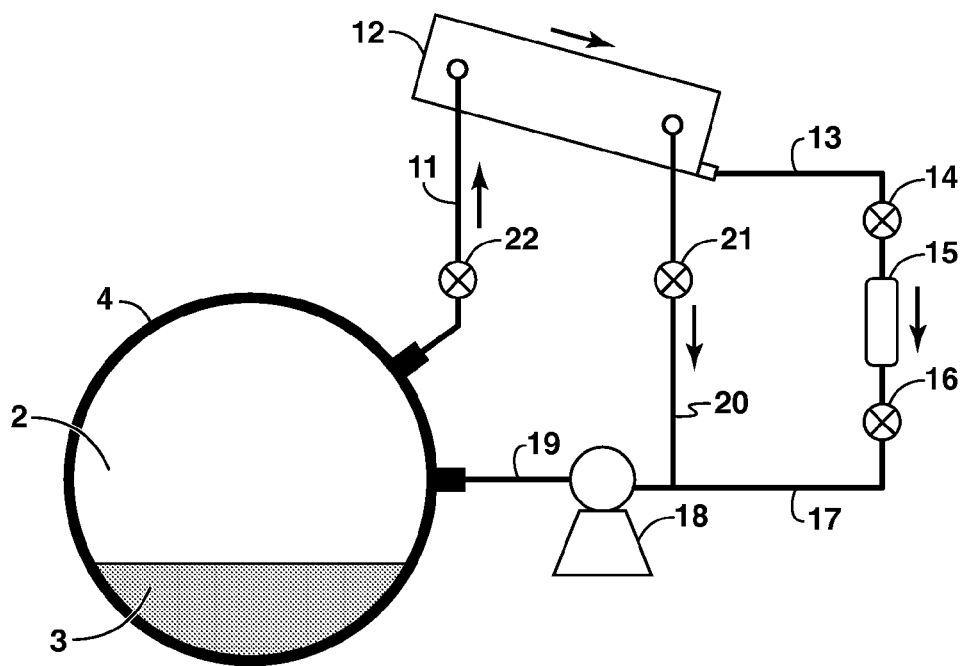
FIG. 3 is a diagram the invention apparatus adapted and affixed to a pipeline for continuous or semi-batch process operation.
Figure 4:
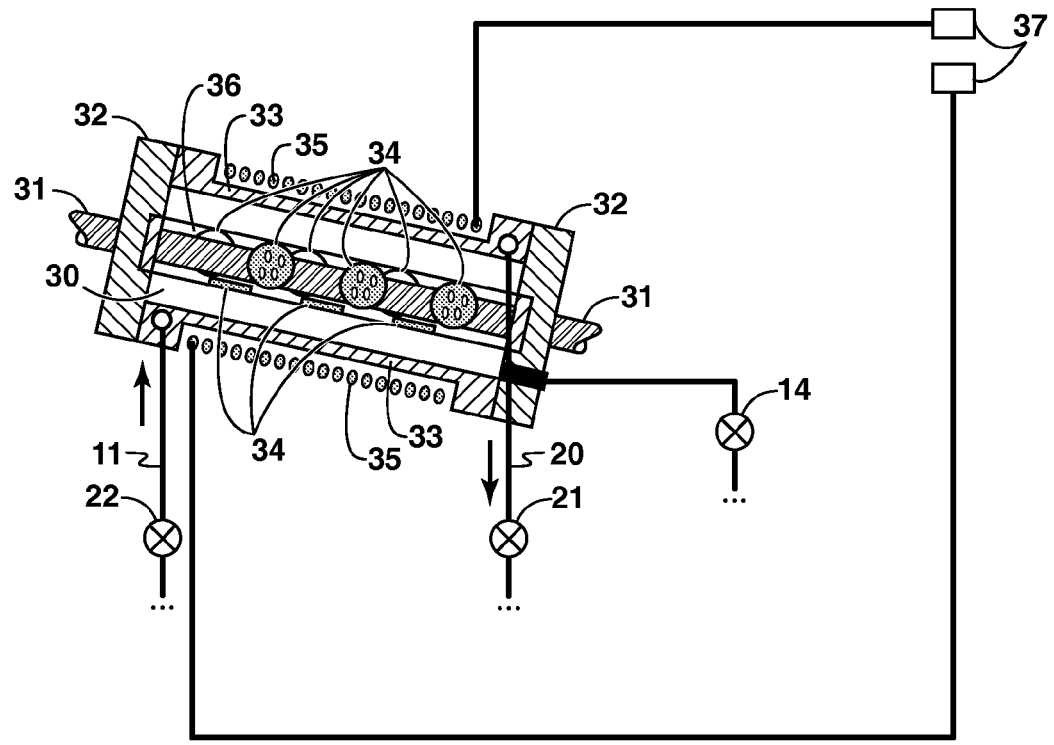
FIG. 4 is a diagrammatic representation of a preferred corrosion testing (TOLC) section useful in the apparatus and process of the invention.

In a preferred embodiment, inside the corrosion test section 12, see FIG. 4, multiple corrosion specimens 34, or coupons, fit into a specimen or coupon holder 36 and are exposed to the saturated vapor. The design of the holder 36 allows the specimens 34 to be cooled from the backside by a chilled coolant line 31 to generate condensation on the specimen 34 faces. Water and a water glycol mixture are typical coolants suitable for cooling. Test section 12 will typically include a pressure housing comprising end sections 32 and hollow flanged weldment body member 33 containing gas chamber 30 into which the vapor from line 11 is passed. The specimen holder 36 may be triangular, cylindrical, rectangular, etc. In addition, the design of the specimen holder 36 allows specimens 34 to be inserted in different orientations that simulate the top, sides, and, optionally, bottom of the pipeline, as illustrated. An optional warming element, illustrated as jacket or coil 35, can be placed outside and around hollow flanged weldment body member 33. This warming element provides for warming said body member for the purpose of preventing additional condensation independent of that on the specimens. A source and return for heating fluid, or electrical energy for heating, are provided through suitable fixtures 37, such as are known and used for typical heating means. In a preferred embodiment, the corrosion test section 12 can be tilted slightly so that the condensation will drain to the bottom of the vessel for collection and removal through the outlet port and line 13 (of FIGS. 2 and 3) leading to cut off valve 14.

In a preferred usage, FIG. 3, where the invention apparatus is adapted for continuous employment online, the autoclave 12 can be replaced by a wet gas pipeline 4, containing a vapor phase 2 comprising the wet natural gas, and a liquid phase 3, constituted of condensed moisture ($H_2O$) plus water soluble gases, gaseous and dissolved acids, and the like (FIG. 1). Here a cutoff valve 22 can be utilized to stop the flow of vapors through the apparatus. The apparatus then is essentially the same as described for FIG. 2. Note that the use of a variable speed pump 18 illustrated is optional and may not be present. Thus the pressure of the wet gas pipeline 4 can be used to supplement or replace pump 18 to transport the uncondensed gas vapor 2 through line 11 to the TOLC test section 12 and through the remainder to the apparatus, ultimately back to the gas line, or as otherwise used or flared. Cutoff valves 16 and 21 can be used to isolate the apparatus from the pipeline 4 when valve 22 is shut.

There are several features of this invention that represent an improvement over existing TOL corrosion apparatus. First, keeping the liquid in a separate vessel from the corrosion test section removes any potential for liquid entrainment to influence test results. Liquid entrainment can make it difficult to measure the condensation rate, and it can alter the environment from true top of the line conditions (condensation from vapor phase alone). Second, the use of specimen/corrosion coupons allows for accurate measurement of weight loss and pitting corrosion. Third, the unique design of the specimen holder allows for simulation of the top versus sides of the pipeline based on the orientation of the specimens. Fourth, the ability to separately control the vapor phase temperature, vapor phase flow rate, and specimen surface temperature allows the condensation rate to be varied over a wide range and held constant for long durations. Condensation rates between 0.002 and 0.5 $g/m^2s$ have been achieved with this apparatus (higher condensation rate are also achievable), and these rates can be held constant for long duration tests. Experiments have been run up to 6 weeks and longer tests are easily achieved. Fifth, the condensation collection and measurement receptacle allows the condensation rates to be measured during the test. Condensation can also be sampled for chemical analysis from this assembly during the test. Lastly, construction of wetted components, other than the specimens, with $H_2S$ resistant materials (e.g., Hastelloy® C-276 from Haynes International, Inc.) allows for high partial pressures of $H_2S$ to be tested.

As noted sour gas ($H_2S$-containing) service preferred embodiments include the use of materials that are resistant to these sour environments. In addition to the Hastelloy® metal, polymeric materials such as polyetheretherketone (PEEK) can also be used. Connection and joint seals can be constructed of $H_2S$ tolerant elastomers such as Viton® and Kalrez® fluoroelastomers (DuPont Performance Elastomers).

For the TOLC test section, the end sections 32 and hollow flanged weldment body member 33 (FIG. 4) make up the primary housing. This component is preferably constructed from the Hastelloy® materials to resist $H_2S$ corrosion and/or cracking. A transparent polymeric housing made from Lucite® may also be used to observe condensation within the TOLC test section. However, the polymeric housing likely will not be able to withstand as severe environments as the metallic one (e.g., temperature, pressure, $H_2S$, etc.).

When a metallic housing is used for the end sections 32 and hollow flanged weldment body member 33, it is possible that condensation may form on the interior of the test section. This additional condensation would make it difficult to accurately measure the condensation rate on the corrosion coupons. Thus, in a preferred embodiment using metallic housing, the exterior of the hollow flanged weldment body member 33 is covered with a warming coil 35 filled with a heated fluid, e.g., glycol/water mixture, to keep the temperature of the test section above that of the saturated vapor. Thus a warming element is preferably around or at least partially around the main body of the corrosion test unit. It is preferred that the warming element/coil and test section be covered with insulation, not depicted, to maintain the elevated temperature. Similarly, it is preferred that the lines connecting the system components also be insulated.

Preferably, the longitudinal cross-section of the specimen/coupon holder is triangular and specimen coupons are located on each face. This allows the coupons to be in oriented to simulate all positions of the interior wall of the pipeline.

Other multi-faceted shapes could be used for the cross-section of the coupon holder. The holder may be constructed from polymeric or metallic materials, as indicated above. A polymeric version made from PEEK helps limit the condensation to the specimens due to the higher thermal conductivity of the steel specimens compared to the polymeric holder material. A metallic version made from the Hastelloy® provides more uniform condensation between the specimens and the holder. This provides a larger surface area over which the condensation forms and leads to a larger volume of condensation compared to a polymeric coupon holder. Thus making it easier to accurately measure low condensation rates. Alternatively, a shaped carbon steel flow element could replace the specimen/coupon holder such that this entire flow element becomes the corrosion specimen. Such may be triangular in shape, cylindrical, rectangular, etc.

Typically chilled glycol/water is used to cool the back of the specimen/coupons to generate condensation on the front face of the coupons, although other known, suitable coolants may be used. It is preferable to use a chiller tube 31 (FIG. 4) that runs through the specimen holder 36 to deliver the chilled glycol water mixture. The specimen holder 36 contains a liquid chamber between the exterior of the chiller tube 31 and the interior of the holder 36 which is filled with a fixed volume of coolant to transfer heat between the holder and the chiller tube. This allows the contents of the chiller tube to be completely contained ensuring that no $H_2S$ can enter the chilled water system even in the event of a seal failure at one or more of specimens 34. In addition, a coolant bypass line (not shown) may be installed to drain the coolant into the TOLC test section 12 at the end of a test for disposal with the liquids in the HPHT autoclave. Since $H_2S$ is a toxic gas, this is a safety feature limiting the possibility of $H_2S$ escaping the system.

Preferably, the optional condensation collection/measurement assembly is made from a high pressure sight glass 15, typically in a Hastelloy® C-276 housing, which is valved off above and below (14, 16). The materials of construction allow operation in $H_2S$ environments. The valves allow for greater flexibility in the operation of the assembly. The valves may be left open to allow condensation to flow through to the vane pump. This may be preferred if high condensation rates could lead to a significant build up within the TOLC test section. The assembly can be valved off to allow condensation to build up in the TOLC test section. This is preferred prior to a condensation measurement to allow a volume of condensation to build up over a fixed time. Opening the lower valve while keeping the top valve closed can help generate a lower pressure in the sight glass. This is useful to help move condensation into the sight glass from the TOLC test section.

A Hastelloy® vane pump is preferred for the gas/liquid pump 18. Such a vane pump can flow gas and/or liquid and can withstand high $H_2S$ partial pressures. A magnedrive system may be used to drive the pump to eliminate any dynamic seals that are in contact with $H_2S$. This is another safety feature to limit the possibility of $H_2S$ escaping the system. Additionally, it's being of a largely explosion proof design allows testing in the presence of hydrocarbons.

Thermocouples (not shown) are used to measure the temperature of the vapor phase in the TOLC test section, the coolant inside the unique coupon holder, and liquid in the HPHT autoclave. A flowmeter (also not shown) measures the flowrate of the saturated vapor through the system. This instrumentation aids in accurately monitoring and controlling the condensation rate in the TOL corrosion apparatus as well as controlling the temperature of the gas.

EXAMPLES

As explained previously, top-of-the-line (TOL) corrosion can occur in wet gas pipelines operating in stratified flow. This corrosion phenomenon occurs when low pH water, devoid of introduced inhibitors that are usually present in the bottom fluids; condenses on the upper half of the pipeline causing severe corrosion.

Sweet natural gas (including $CO_2$ only) TOL corrosion has been investigated extensively in the literature and testing apparatus and models have been developed to predict its presence. These models are based on the premise that in $CO_2$ dominated systems, TOL corrosion is limited by the amount of iron which can be dissolved in the condensing water. These models are also known as supersaturation models. As iron is dissolved in the condensing water the pH is increased leading to the possibility of iron carbonate formation which protects the steel. However, these models do not apply to sour systems (containing $H_2S$) where the dominant corrosion scale is based on iron sulfides. There has been very little work published on sour TOL corrosion limited to very low levels of $H_2S$ and testing apparatus to simulate its mechanisms have not been available. In addition the presence of co-condensing hydrocarbon and water phase on top of the line corrosion apparently has not been investigated in the literature to date.

Figure 5:
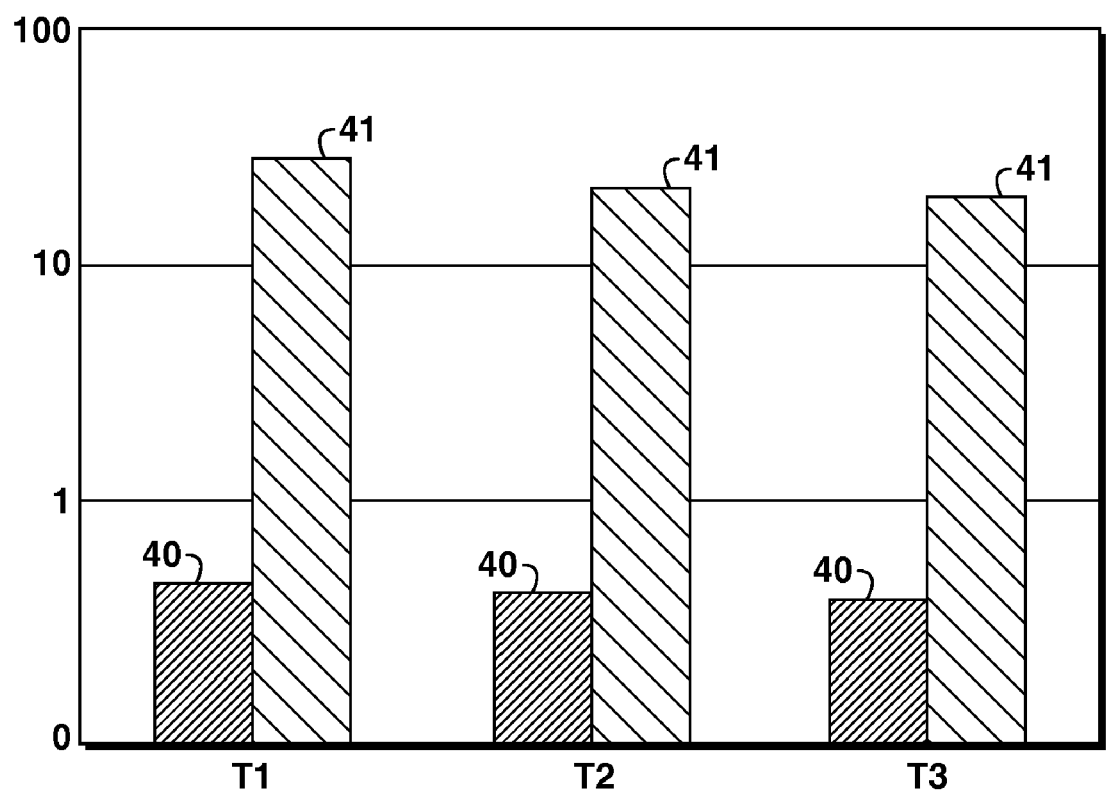
FIG. 5 presents graphical data obtained that compares simulated TOL corrosion to actual corrosion observed for sour, wet gas.

The data represented in FIG. 5 was generated in the top of the line corrosion apparatus of the invention at low condensation rates over a period of six weeks. The vertical axis represents the TOL corrosion rate as measured in mpy (mils per year). The columns, T1-T3, represent three experimental tests 1-3. The gas composition was the same for all three experiments, each containing ~9 psi partial pressure of $H_2S$ (~62 kPa) and 24 psi (165.5 kPa) partial pressure of $CO_2$. However, the three tests contained different levels of organic acids. The experiments maintained a constant condensation rate of 0.002 ml/$m^2$s throughout the six week tests. Measured sour TOL corrosion rates are compared to those predicted using the deWaard and Milliams TOL corrosion correction factor based on test data developed with test apparatus that only allows testing with $CO_2$. In FIG. 5 the cross-hatched areas 40 represent the values obtained using this supersaturated model. The non-cross-hatched areas 41 illustrate the results using the TOLC testing methods according to the invention. The data clearly shows that TOL corrosion rates in sour environments can be high under low condensation conditions and that existing test apparatus that only allow testing with $CO_2$ and low levels of $H_2S$ fail to simulate sour gas TOL corrosion.

Further, Table 1, below, illustrates a typical series of conditions along the length of a wet gas pipeline. The data shown were calculated from commercially available modeling software Olga Scandpower Software using field observed conditions. Olga is Norwegian petroleum software originally developed by IFE for Statoil in 1983. Olga 2000 is capable of one dimensional simulation of Oil, gas and water flows. See, e.g., *The dynamic Two-Fluid Model Olga Theory and application* by Bendiksen, K. H Malnes, D. Moe, R. and S, Nuland edited by SPE Production Engineering, May 1991, pp. 171-180. Such software can calculate variations in temperature, pressure, flow rate, flow regime, and amounts of phases present along the length of a pipeline based on inlet conditions and the pipeline configuration. Column A shows the distance in meters along a wet gas pipeline, column B gives the variation in liquid/pipeline wall temperature in degrees Centigrade, column C gives a typical ambient temperature in the environment surrounding the pipeline and the external surface of the pipeline, and column D provides the calculated condensation rate in grams per m²-sec, all as a function of the distance traveled along the pipeline from its source. The difference in temperature between columns B and C illustrates the temperature gradient across the pipe wall, which drives condensation inside the pipeline. The condensation rates in Column D are typically not calculated directly by flow modeling software, but these can be calculated by the difference in the amount of water between two locations (a typical output of flow modeling software), assuming that the water drops out as condensation on the top half of the pipe wall. Higher condensation rates are typically observed when higher temperature gradients across the pipe wall are present, and the condensation rate approaches zero as the internal pipeline temperature approaches the ambient temperature (i.e., the temperature gradient approaches zero). The results of such modeling may be used to set conditions (gas temperature, coupon temperature, and condensation rate) inside the TOL corrosion apparatus described herein.

TABLE 1

| Distance (m) | Internal temperature (° C.) | Ambient temperature (° C.) | Condensation rate (g/m²-s) |
|---|---|---|---|
| 500 | 54.0 | 23.9 | 0.5454 |
| 1,000 | 47.2 | 23.9 | 0.3315 |
| 1,500 | 41.9 | 23.9 | 0.2122 |
| 2,000 | 37.8 | 23.9 | 0.1404 |
| 2,500 | 34.6 | 23.9 | 0.0968 |
| 3,000 | 32.2 | 23.9 | 0.0677 |
| 3,500 | 30.3 | 23.9 | 0.0500 |
| 4,000 | 28.8 | 23.9 | 0.0358 |
| 4,500 | 27.7 | 23.9 | 0.0261 |
| 5,000 | 26.8 | 23.9 | 0.0191 |
| 5,500 | 26.1 | 23.9 | 0.0143 |
| 6,000 | 25.6 | 23.9 | 0.0107 |
| 6,500 | 25.2 | 23.9 | 0.0077 |
| 7,000 | 24.9 | 23.9 | 0.0060 |
| 7,500 | 24.7 | 23.9 | 0.0043 |
| 8,000 | 24.5 | 23.9 | 0.0034 |
| 8,500 | 24.3 | 23.9 | 0.0024 |
| 9,000 | 24.2 | 23.9 | 0.0015 |
| 9,500 | 24.1 | 23.9 | 0.0011 |
| 10,000 | 24.1 | 23.9 | 0.0008 |
| 10,500 | 24.0 | 23.9 | 0.0002 |
| 11,000 | 24.0 | 23.9 | 0.0002 |
| 11,500 | 23.9 | 23.9 | 0.0000 |
| 12,000 | 23.9 | 23.9 | 0.0000 |
| 12,500 | 23.9 | 23.9 | 0.0000 |
| 13,000 | 23.9 | 23.9 | 0.0000 |
| 13,500 | 23.9 | 23.9 | 0.0000 |
| 14,000 | 23.9 | 23.9 | 0.0000 |
| 14,500 | 23.9 | 23.9 | 0.0000 |
| 15,000 | 23.9 | 23.9 | 0.0000 |

We claim:

1. A method for determining corrosion in wet gas pipelines comprising:
    a) collecting or replicating a portion of the liquid phase from a wet gas pipeline;
    b) placing said portion in a high pressure, high temperature autoclave along with equivalent partial pressures of acid gases, and heating it to prepare a saturated vapor phase within said autoclave;
    c) transferring at least a portion of the saturated vapor to a corrosion test unit comprising a gas inlet port, a specimen holder section, one or more corrosion testing specimens arranged in said specimen holder section, a liquid collection outlet port, and a gas return line via a variable speed pump to the autoclave of b), said specimen holder section having external, temperature adjustable means;
    d) chilling said specimen holder section so as to cause condensation from said vapor phase onto said corrosion testing specimens;
    e) warming the body member of said test unit to prevent condensation independent of that on the specimens, and
    f) draining and withdrawing at least a portion of the vapor after subjected to condensation chilling in the corrosion test unit for return to the autoclave via the variable speed pump,
    g) measuring the volume of said condensation in a liquid collection and measuring unit connected at the inlet side said unit to the outlet port before returning said condensation via said pump to said autoclave, and
    h) calculating a value selected from the group consisting of corrosions rate, pitting of the specimen, weight loss of the specimen, and any combination thereof.

2. The method of claim 1 wherein the specimen holder is configured to allow specimens to be inserted in different orientations that simulate a portion of the pipeline selected from the group consisting of a top portion of the pipeline, a side portion of the pipeline, a bottom portion of the pipeline, and any combination thereof.

3. The method of claim 2 comprising arranging said specimens in a triangular specimen holder section.

4. The method of claim 1, further comprising using a shaped carbon steel flow element as a single corrosion testing specimen.

5. The method of claim 1, further comprising the step of periodically halting the flow of vapor from the autoclave to the corrosion testing unit, and measuring said corrosion testing plates for calculating the one or more values of step e), and replacing with new specimens or specimen section as needed.

6. The method of claim 1 wherein said external, temperature adjustable means comprises a chilled coolant line.

7. A method for determining corrosion in wet gas pipelines comprising the steps of:
    a) collecting a portion of the vapor phase from a wet gas pipeline,
    b) transferring at least a portion of the vapor phase collected in a) to a corrosion test unit comprising an gas inlet port, a specimen holder section, one or more corrosion testing specimens arranged in said specimen holder section, a liquid collection outlet port, said specimen holder section having external, temperature adjustable means, wherein the inlet side of the liquid collection and measuring unit is connected to the liquid collection outlet port,
    c) chilling said specimen holder section so as to cause condensation from said vapor phase onto said corrosion testing specimens,
    d) warming the body member of said test unit to prevent condensation independent of that on the specimens, and
    e) withdrawing from said corrosion test unit at least a portion of the vapor phase after the vapor phase is subjected to condensation chilling for return to an autoclave,
    f) draining and withdrawing said condensation via said liquid collection outlet port, g) measuring the volume of said condensation m a liquid collection and measuring unit, h) returning said condensation via a pump to the autoclave, and i) halting periodically the flow of vapor from the pipeline to the corrosion testing unit, and inspecting said corrosion testing plates, replacing with new specimens or specimen section as needed.

8. The method of claim 7, additionally comprising using a variable speed pump to transfer or assist transfer the vapor phase from the corrosion test unit in step e).

9. The method of claim 7, wherein said external, temperature adjustable means comprises a chilled coolant line.

10. An apparatus suitable for determining corrosion in wet gas pipelines comprising:

a) a high pressure, high temperature autoclave;

b) a corrosion test unit comprising a gas inlet port, a specimen older section, a plurality of corrosion testing specimens affixed on said specimen older section, a liquid collection outlet port, and a gas return line to the autoclave a), said specimen holder section having external, temperature adjustable means, and a warming element placed around or at least partially around the main body of the corrosion test unit;

c) a liquid collection and measuring unit, the inlet side of the collection and measuring unit connected to the liquid outlet port in the corrosion test unit b) and at the outlet side to a variable speed pump.

11. The apparatus of claim 10, wherein said external, temperature adjustable means comprises a chilled coolant line.

12. The apparatus of claim 10, wherein said apparatus is adapted for continuous employment by installation on a wet gas pipeline which pipeline replaces the autoclave a).

13. The apparatus of claim 12 additionally comprising a warming element placed around or at least partially around the main body of the corrosion test unit.

14. An apparatus suitable for determining corrosion in wet gas pipelines comprising:

a) a high pressure, high temperature autoclave;

b) a corrosion test unit comprising a gas inlet port, a specimen holder section, a plurality of corrosion testing specimens affixed on said specimen holder section, a liquid collection outlet port, and a gas return line to the autoclave a), said specimen holder section having external, temperature adjustable means c) a warming element placed around or at least partially around the main body of the corrosion test unit, wherein the warming element and test section are insulated.

15. The apparatus of claim 14, additionally comprising a liquid collection and measuring unit connected at the liquid outlet port in the corrosion test unit b).

16. An apparatus suitable for determining corrosion in a wet gas pipeline comprising:

a) a corrosion test unit comprising a gas inlet port, a specimen holder section, a plurality of corrosion testing specimens affixed on said specimen holder section, a liquid collection outlet port, and a gas return line to the wet gas pipeline, said specimen holder section having external, temperature adjustable means, wherein said apparatus is installed on the wet gas pipeline, and a variable speed pump is installed for the purpose of transporting or assisting returning the uncondensed gas vapor to the pipeline.

17. An apparatus suitable for determining corrosion in a wet gas pipeline comprising:

a) a corrosion test unit comprising a gas inlet port, a specimen holder section, a plurality of corrosion testing specimens affixed on said specimen holder section, a liquid collection outlet port, and a gas return line to the wet gas pipeline, said specimen holder section having external, temperature adjustable means, and b) a warming element placed around or at least partially around the main body of the corrosion test unit, where the warming element and test section are insulated wherein said apparatus is adapted for continuous employment by installation on a wet gas pipeline.

* * * * *